US006931280B1

(12) United States Patent
Yang

(10) Patent No.: US 6,931,280 B1
(45) Date of Patent: Aug. 16, 2005

(54) APPARATUS AND METHOD FOR BI-VENTRICULAR PACING AND SENSING IN AN IMPLANTABLE DEVICE

(75) Inventor: Weiqun Yang, Cupertino, CA (US)

(73) Assignee: Pacesetter, Inc., Sunnyvale, CA (US)

(*) Notice: Subject to any disclaimer, the term of this patent is extended or adjusted under 35 U.S.C. 154(b) by 559 days.

(21) Appl. No.: 10/074,403

(22) Filed: Feb. 11, 2002

(51) Int. Cl.[7] .............................................. A61N 1/365
(52) U.S. Cl. ....................................................... 607/9
(58) Field of Search ............................ 607/2, 7, 9, 13, 607/27, 99, 148, 14

(56) References Cited

U.S. PATENT DOCUMENTS

| | | | |
|---|---|---|---|
| 4,928,688 A | 5/1990 | Mower ................. 128/419 PG |
| 4,991,583 A * | 2/1991 | Silvian ......................... 607/13 |
| 6,185,459 B1 * | 2/2001 | Mehra et al. .................. 607/14 |
| 6,324,425 B1 | 11/2001 | Blow et al. .................... 607/13 |
| 6,363,278 B1 | 3/2002 | Stahmann et al. ............. 607/9 |

* cited by examiner

Primary Examiner—George Manuel
(74) Attorney, Agent, or Firm—Steven M. Mitchell

(57) ABSTRACT

An apparatus and method for pacing and sensing the right side as well as the left side of the heart (bi-ventricular pacing and sensing). The bi-ventricular pacing and sensing is accomplished by introducing an additional dedicated pacing and sensing path for the left ventricle of the heart. Two additional terminals are added to the pacing and sensing path for the left ventricle to enable pacing and sensing in the left ventricle of the heart. In addition, switches are added to the pacing path for the left ventricle of the heart. The switches are controlled by a programmable controller and allow the selection of the desired ventricle(s) in which pacing is to occur.

15 Claims, 11 Drawing Sheets

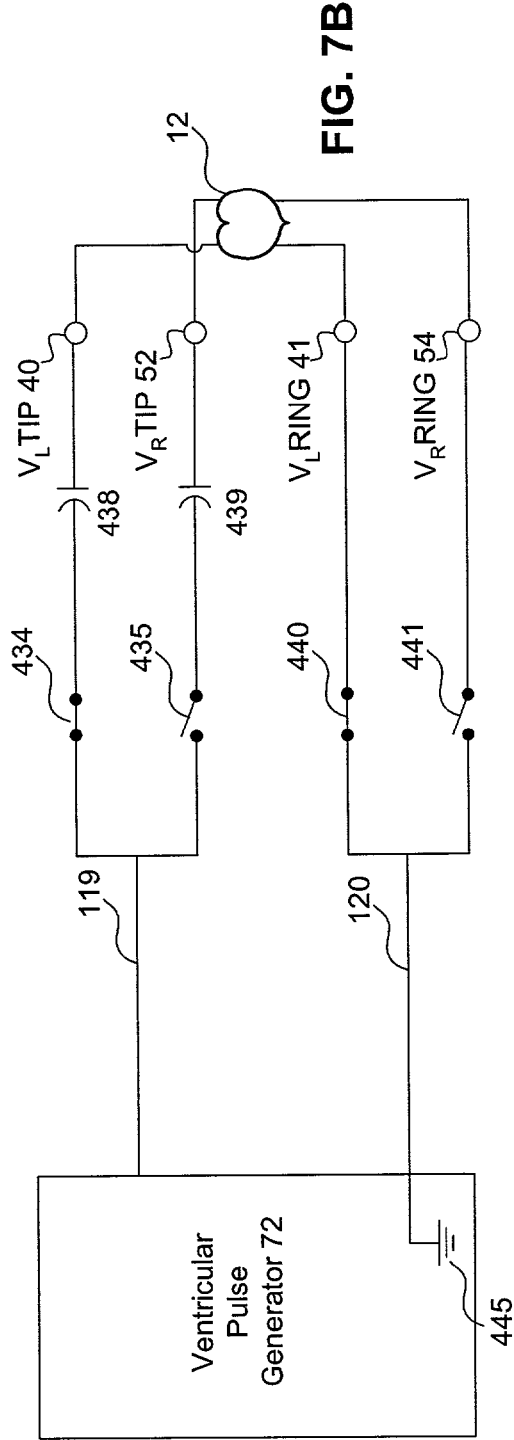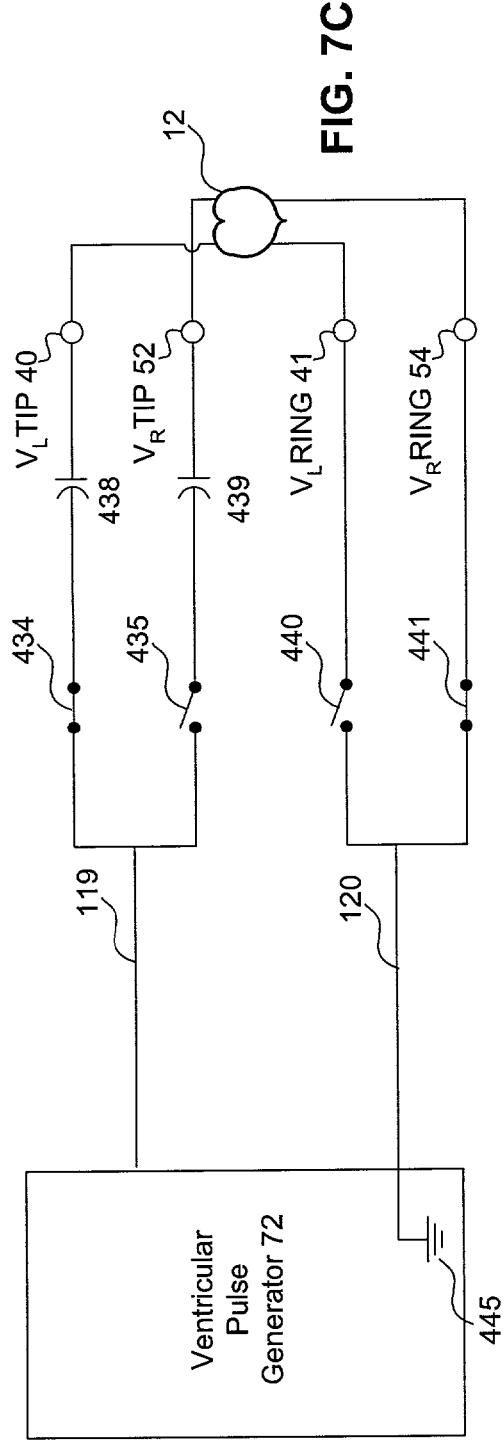

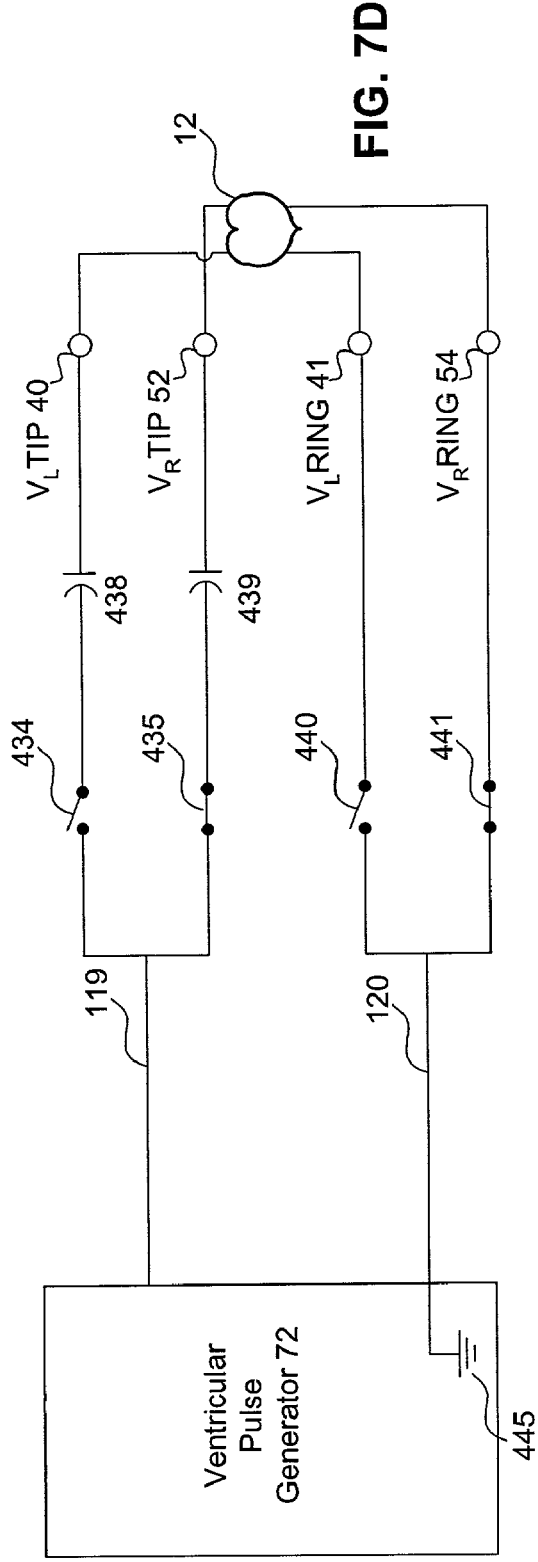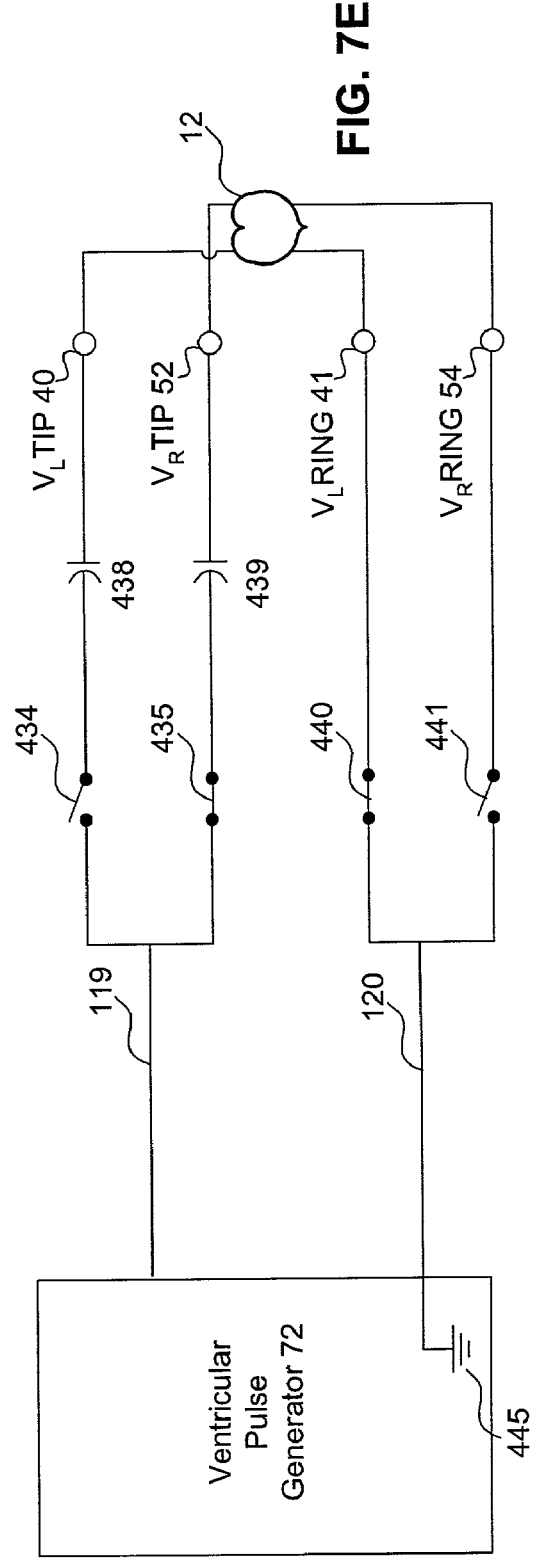

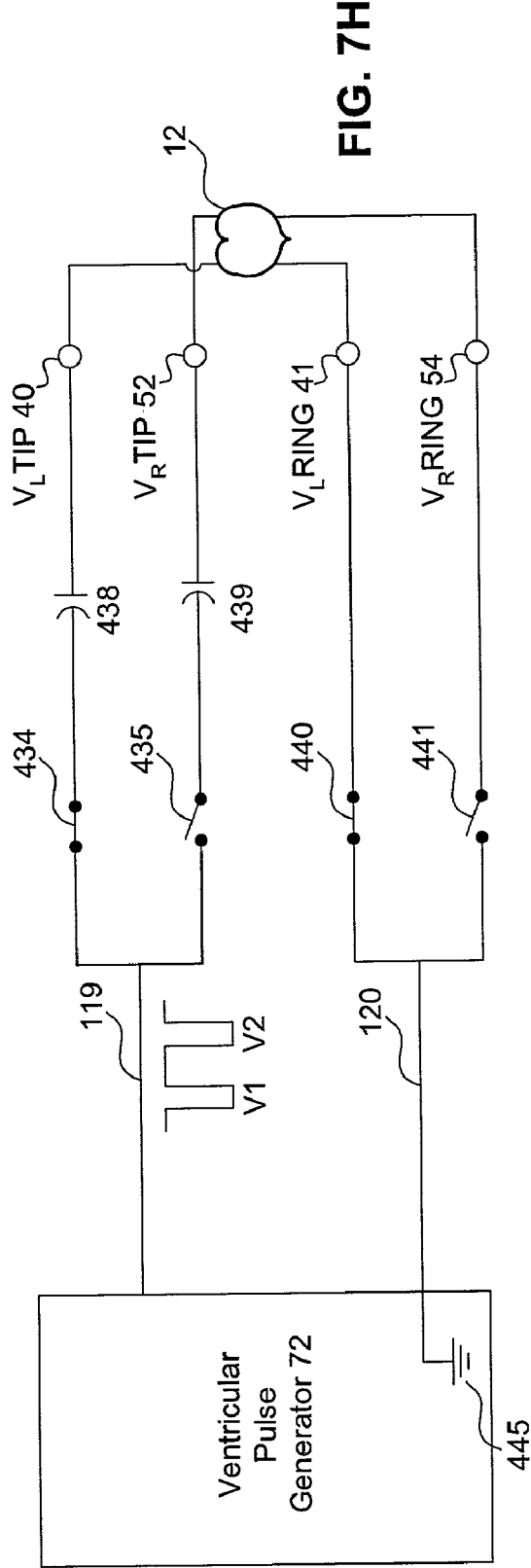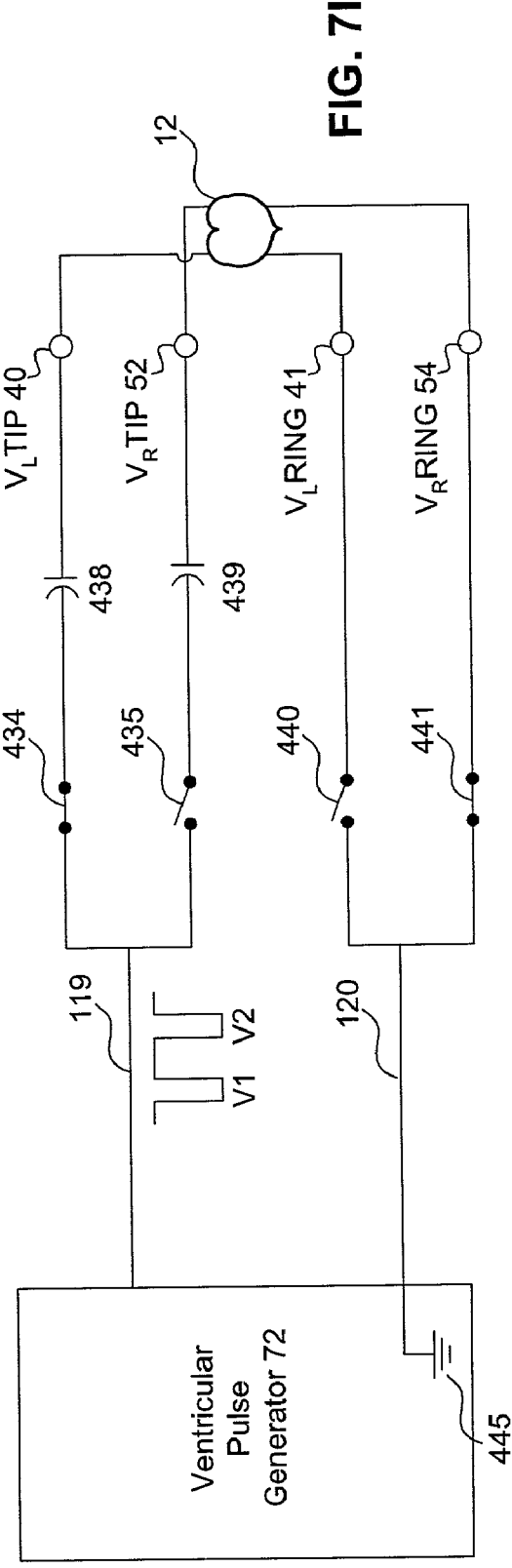

APPARATUS AND METHOD FOR BI-VENTRICULAR PACING AND SENSING IN AN IMPLANTABLE DEVICE

BACKGROUND OF THE INVENTION

1. Field of the Invention

The present invention relates generally to implantable cardiac stimulation devices. More particularly, the present invention relates to an apparatus and method for pacing a heart in its right ventricle or left ventricle as well as pacing the heart in both ventricles.

2. Related Art

Implantable cardiac stimulation devices are well known in the art. Such devices may include, for example, implantable cardiac pacemakers and defibrillators either alone or combined in a common enclosure. The devices are generally implanted in a pectoral region of the chest beneath the skin of a patient within what is known as a subcutaneous pocket. The implantable devices generally function in association with one or more electrode carrying leads which are implanted within the heart. The electrodes are positioned within the heart for making electrical contact with the muscle tissue of their respective heart chamber. Conductors within the leads couple the electrodes to the device to enable the device to deliver the desired electrical therapy.

Traditionally, therapy delivery has been limited to the right portion of the heart. However, new lead structures and methods have been produced and practiced for also delivering cardiac rhythm management therapy from or to the left portion of the heart. For example, it has been demonstrated that electrodes placed in the coronary sinus and great vein may be used for left atrial pacing, left ventricular pacing, cardioversion and defibrillation. These advancements enable implantable cardiac stimulation devices to address the needs of the wide patient population, from those that would benefit from right heart side pacing alone, to those that would benefit from left heart side pacing in conjunction with right heart side pacing (bi-chamber pacing), to those that would benefit from left heart side pacing alone.

For instance, ideally, the left and right ventricle of the heart should contract in the same time frame. A large portion of the population, however, has an enlarged left side of the heart. This enlargement results in failure of the left ventricle to contract with the right ventricle (that is, the contraction of the left ventricle is delayed). Thus, to obtain ventricular synchronization, the left ventricle needs to be stimulated to ensure synchronous contraction of the ventricles.

Therefore, what is needed is an apparatus and method for bi-ventricular pacing of the heart.

SUMMARY OF THE INVENTION

The present invention is directed towards a method and electrical configuration apparatus for use in a cardiac stimulation device. The cardiac stimulation device includes a pulse generator. In one embodiment, the electrical configuration apparatus includes a first switch for connecting an output path of the pulse generator to a first terminal, wherein the first terminal is adapted for connection to a first implantable electrode. The electrical configuration apparatus also includes a second switch for connecting the output path of the pulse generator to a second terminal, wherein the second terminal is adapted for connection to a second implantable electrode. In an embodiment, the electrical configuration apparatus further includes a third switch for connecting a third terminal to a ground, wherein the third terminal is adapted for connection to a third implantable electrode. This embodiment also includes a fourth switch for connecting a fourth terminal to the ground, wherein the fourth terminal is adapted for connection to a fourth implantable electrode. The various switches are controlled by a controller to be open or closed to allow a pulse generated by the pulse generator to be transmitted to whichever terminal is to receive the pulse. Thus, the microcontroller can selectively control which ventricle of the heart (i.e., the right ventricle, the left ventricle, or both) will be paced by the pulse. In addition, the microcontroller can selectively control which ventricle of the heart will be sensed by executing measurements between selected terminals. The present invention offers advantages such as the capability to deliver independent pacing pulses to each of the ventricles with a programmable delay (for example, a delay of 10–70 ms) between pacing pulses delivered to the right ventricle and the left ventricle. The present invention also offers the advantage of the capability to deliver pacing pulses of varying pulse amplitudes and/or pulse widths.

BRIEF DESCRIPTION OF THE FIGURES

Further features and advantages of the present invention may be more readily understood by reference to the following description taken in conjunction with the accompanying drawings, in which:

FIGS. 7A–7I are circuit diagrams illustrating various pacing configurations that can be realized with the present invention.

DETAILED DESCRIPTION OF THE PREFERRED EMBODIMENTS

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

Exemplary Stimulation Device

Figure 1:
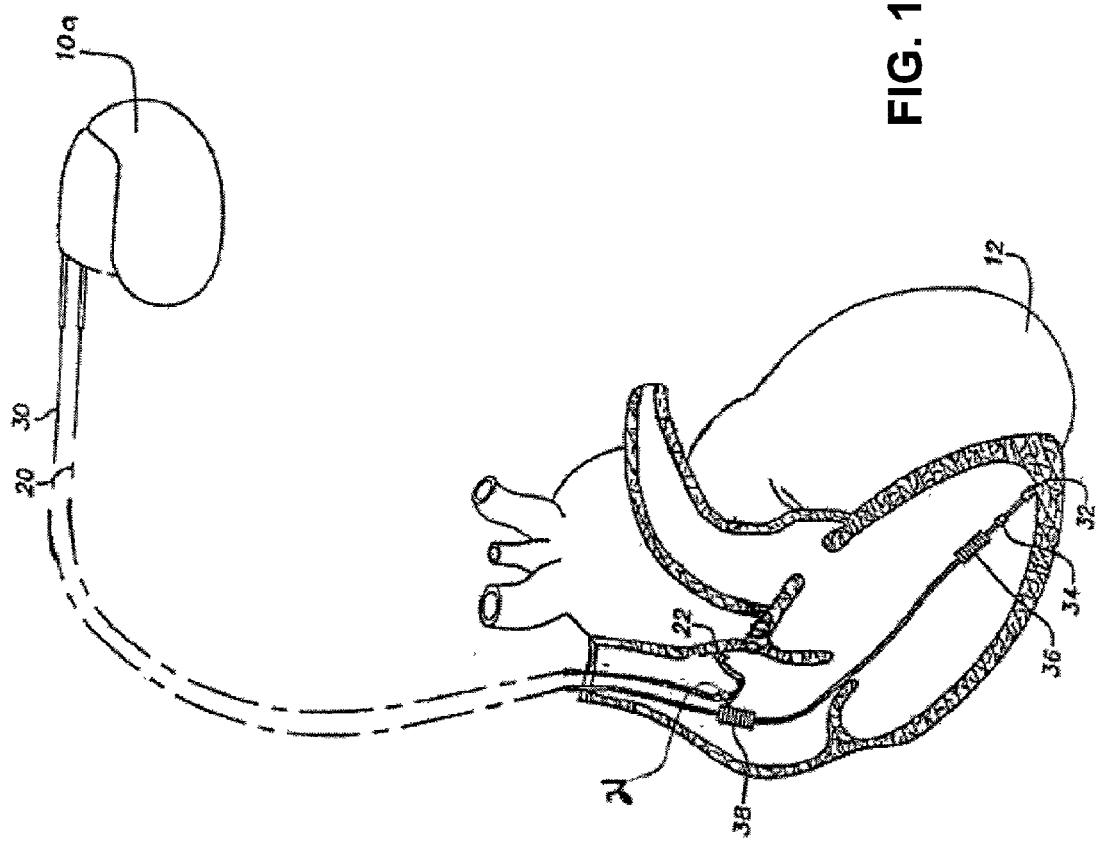
FIG. 1 is a simplified diagram illustrating an implantable stimulation device in electrical communication with two leads implanted into a patient's heart for delivering stimulation and shock therapy to the right side of the heart.

FIG. 1 illustrates an exemplary stimulation device 10a (also referred to as a pacing device, or a pacing apparatus) in electrical communication with a patient's heart 12 by way of two leads, 20 and 30, suitable for delivering stimulation and shock therapy to the right side of the heart 12. Without modification, stimulation device 10a is capable of pacing and sensing in the right side of the heart only. To sense atrial cardiac signals and to provide right atrial chamber stimulation therapy, the stimulation device 10a is coupled to an implantable right atrial lead 20 having at least an a right atrial tip electrode 22, which typically is implanted in the patient's right atrial appendage. A right atrial ring electrode 21 is also shown.

The stimulation device 10a is also shown in electrical communication with the patient's heart 12 by way of an implantable right ventricular (RV) lead 30 having, in this embodiment, a right ventricular tip electrode 32, a right ventricular ring electrode 34, a right ventricular coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
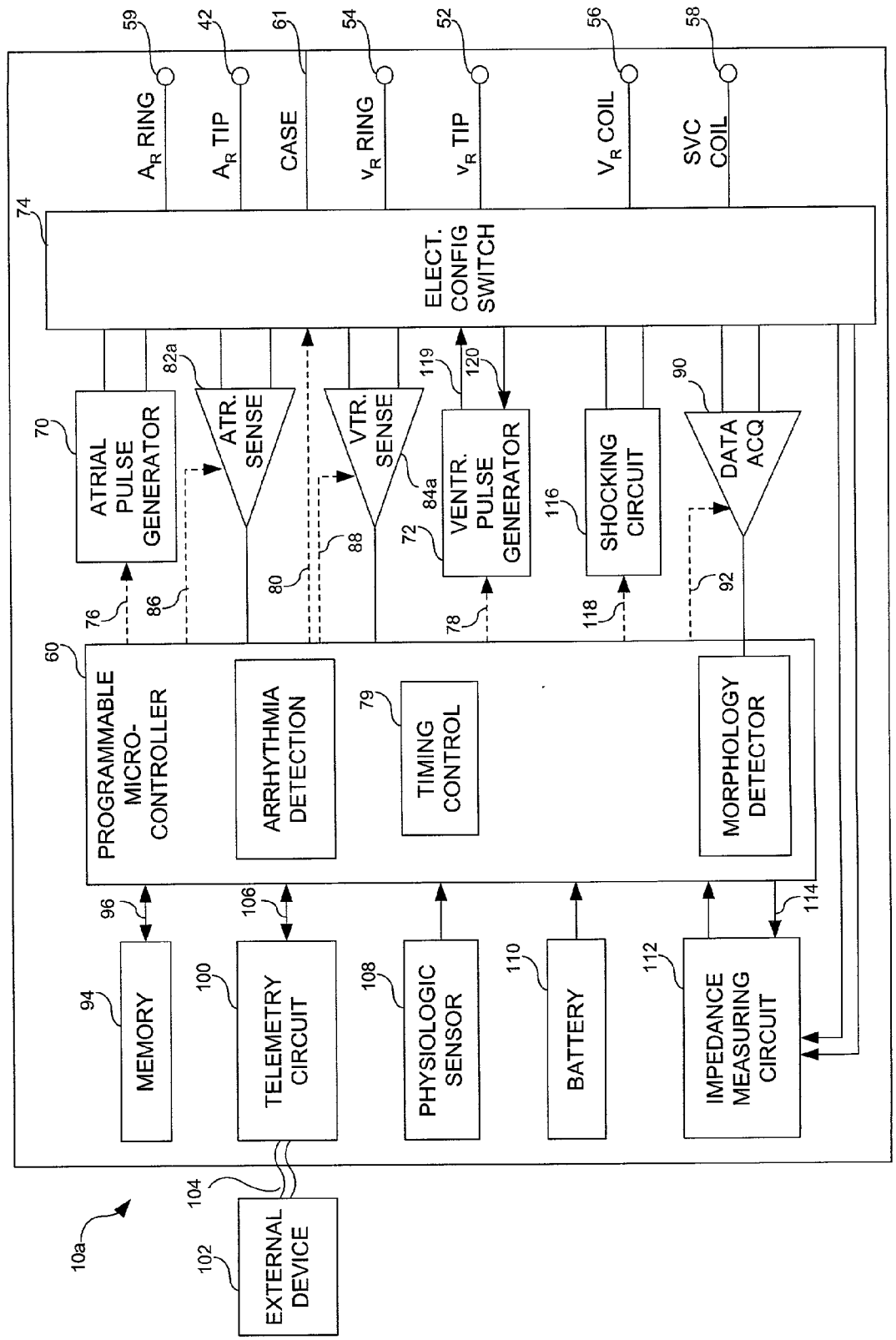
FIG. 2 is a functional block diagram of an implantable stimulation device illustrating the basic elements of a stimulation device which can provide cardioversion, defibrillation and pacing stimulation to the right side of the heart.

FIG. 2 illustrates a simplified block diagram of the implantable stimulation device 10a of FIG. 1, which is capable of treating both fast and slow arrhythmias with stimulation therapy to the right side of the heart 12, including cardioversion, defibrillation, and pacing stimulation. The device shown in FIG. 2 is not adapted for bi-ventricular pacing and sensing. For example, in the device shown in FIG. 2, pacing can only occur in the right ventricle of the heart 12. Pacing in the left ventricle of the heart 12 can be accomplished by certain modifications, however. But certain modifications (for example, tying certain electrode leads) prevent the realization of certain advantages of the bi-ventricular pacing and sensing method of the present invention (described below).

The housing for the stimulation device 10a, shown schematically in FIG. 2, is often referred to as the "can", "case" or "case electrode" (illustrated as 61 in FIG. 2) and may be programmably selected to act as the return electrode for all "unipolar" modes. The housing may further be used as a return electrode alone or in combination with one or more of the coil electrodes 36 and 38, for shocking purposes. The housing further includes a connector (not shown) having a plurality of terminals, 42, 52, 54, 56, 58, and 59 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the right atrial tip electrode 22. The connector also includes a right atrial ring terminal ($A_R$ RING) 59 adapted for connection to the right atrial ring electrode 21.

To support right ventricular sensing and pacing, the connector further includes a right ventricular tip terminal ($V_R$ TIP) 52, which is adapted for connection to the right ventricular tip electrode 32. The connector also includes a right ventricular ring terminal ($V_R$ RING) 54, which is adapted for connection to the right ventricular ring electrode 34, a right ventricular shocking terminal ($R_V$ COIL) 56, which is adapted for connection to the SVC coil electrode 38, and an SVC shocking terminal (SVC COIL) 58, which is adapted for connection to the RV coil electrode 36.

At the core of the stimulation device 10a is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art. In a specific embodiment of the present invention, the microcontroller 60 performs some or all of the steps associated with controlling switches in accordance with the present invention. Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

Still referring to FIG. 2, an atrial pulse generator 70 and a ventricular pulse generator 72 generate pacing stimulation pulses for delivery by the right atrial lead 20 and the right ventricular lead 30. It is understood that in order to provide stimulation therapy to the right ventricle of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control pacing parameters (for example, the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular (AV) delay, interventricular (RV-LV) delay, atrial interconduction (A—A) delay, ventricular interconduction (V—V) delay, and pacing rate.

The electrical configuration switch 74 includes a plurality of switches for connecting the desired electrodes to the appropriate I/O circuits, thereby providing complete electrode programmability. The electrical configuration switch 74 can be any switching device. For example, the switch can be a semiconductor switch (e.g., a transistor circuit) or can be a micro relay. Accordingly, the switch 74, in response to a control signal 80 from the microcontroller 60, determines the polarity of the stimulation pulses (for example, unipolar, bipolar, combipolar, etc.) by selectively closing the appropriate combination of switches (not shown in FIG. 2).

Atrial (ATR. SENSE) and ventricular (VTR. SENSE) sensing circuits, 82a and 84a, respectively, may include dedicated sense amplifiers, multiplexed amplifiers, or shared amplifiers. It will be apparent to one skilled in the relevant art(s) that each of the atrial and ventricular sensing circuits, 82a and 84a, respectively, can be analog or digital. If the circuit is digital, it will include an analog-to-digital front-end. The switch 74 determines the "sensing polarity" of the cardiac signal by selectively closing the appropriate switches. In this way, the clinician may program the sensing polarity independent of the stimulation polarity.

Each sensing circuit, 82a and 84a, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10a to deal effectively with the difficult problem of sensing the low amplitude signal characteristics of atrial or ventricular fibrillation. Such sensing circuits, 82a and 84a, can be used to determine cardiac performance values used in the present invention.

The outputs of the atrial and ventricular sensing circuits, 82a and 84a, are connected to the microcontroller 60 which, in turn, is able to trigger or inhibit the atrial and ventricular pulse generators, 70 and 72, respectively, in a demand fashion in response to the absence or presence of cardiac activity, in the appropriate chambers of the heart 12. The sensing circuits, 82a and 84a, in turn, receive control signals over signal lines, 86 and 88, from the microcontroller 60 for purposes of measuring cardiac performance at appropriate times, and for controlling the gain, threshold, polarization charge removal circuitry (not shown), and timing of any blocking circuitry (not shown) coupled to the inputs of the sensing circuits, 82a and 86a.

For arrhythmia detection, the device 10a utilizes the atrial and ventricular sensing circuits, 82a and 84a, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of data acquisition system 90. It will be apparent to one skilled in the relevant art(s) that the data acquisition system 90 can be an analog or a digital system. If the system is digital, it will include an analog-to-digital front-end. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20 and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart 12 is of sufficient energy to depolarize the cardiac tissue, thereby causing the heart 12 to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10a to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10a may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10a (as contained in the microcontroller 60 or memory 94) to be sent to an external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In one embodiment, the stimulation device 10a further includes a physiologic sensor 108, that can be used to detect changes in cardiac performance or changes in the physiological condition of the heart 12. Accordingly, the microcontroller 60 can respond by adjusting the various pacing parameters (such as rate, AV Delay, RV-LV Delay, V—V Delay, etc.) in accordance with the embodiments of the present invention. The microcontroller 60 controls adjustments of pacing parameters by, for example, controlling the stimulation pulses generated by the atrial and ventricular pulse generators, 70 and 72. While shown as being included within the stimulation device 10a, it is to be understood that the physiologic sensor 108 may also be external to the stimulation device 10a, yet still be implanted within or carried by the patient. More specifically, the sensor 108 can be located inside the device 10a, on the surface of the device 10a, in a header of the device 10a, or on a lead (which can be placed inside or outside the bloodstream).

The stimulation device 10a additionally includes a battery 110 which provides operating power to all of the circuits shown in FIG. 2. For the stimulation device 10a, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10a preferably employs lithium/silver vanadium oxide batteries, as is true for most (if not all) current devices.

The stimulation device 10a further includes a magnet detection circuitry (not shown), coupled to the microcontroller 60. The purpose of the magnet detection circuitry is to detect when a magnet is placed over the stimulation device 10a. The magnet may be used by a clinician to perform various test functions of the stimulation device 10a and/or to signal the microcontroller 60 when the external device 102 is in place to receive or transmit data to the microcontroller 60 through the telemetry circuits 100.

Still referring to FIG. 2, the device 10a is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the present invention and is shown only for completeness.

In the case where stimulation device 10a is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the RV coil electrode 36, and/or the SVC coil electrode 38. As noted above, case 61 may act as an active electrode in combination with one or more electrodes.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, the microcontroller 60 is capable of controlling the synchronous or asynchronous delivery of the shocking pulses.

Figure 3:
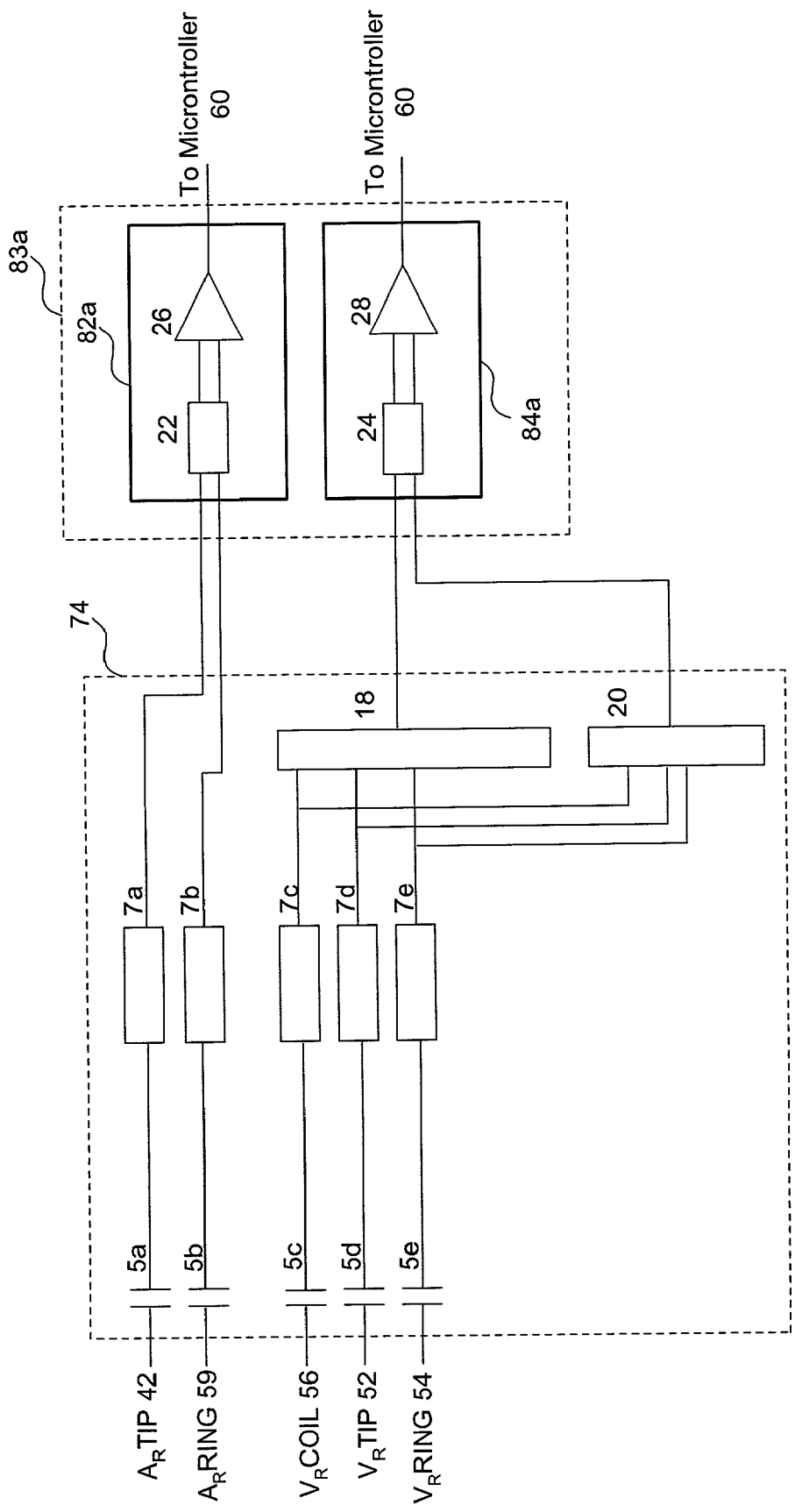
FIG. 3 is a circuit diagram of the electrical configuration switch and sense circuits of an implantable stimulation device capable of sensing in the right side of the heart.

FIG. 3 is an exemplary circuit diagram of a portion of electrical configuration switch 74 and sensing circuitry 83a, both located within the stimulation device 10a. Terminals $A_R$ TIP 42, $A_R$ RING 59, $V_R$ COIL 56, $V_R$ TIP 52, and $V_R$ RING 54 are also located within the stimulation device 10a, as shown in FIG. 2.

Electrical configuration switch 74 comprises capacitors 5, RF filters 7 and input multiplexors 18 and 20. The sensing circuitry 83a shown in FIG. 3 is adapted for sensing on the right side of the heart. The sensing circuitry 83a comprises atrial sensing circuitry 82a and ventricular sensing circuitry 84a. The atrial sensing circuitry 82a comprises passive filter 22 and amplifier 26. The ventricular sensing circuitry 84a comprises passive filter 24 and amplifier 28.

Operation of the sensing circuitry 83a will now be described in conjunction with operation of the electrical configuration switch 74.

Each one of the terminals $A_R$ TIP 42, $A_R$ RING 59, $V_R$ COIL 56, $V_R$ TIP 52, and $V_R$ RING 54 is connected to its respective electrode located in the heart 12. For example, as discussed above, $V_R$ TIP 52 is adapted for connection to right ventricular tip electrode 32 located within the heart 12. Each one of the terminals relays cardiac activity generated by the heart 12 to stimulation device 10a. More specifically, each one of the electrodes within the heart 12 receives a particular cardiac signal from its respective region of the heart 12 and relays this signal to the associated one of the terminals in stimulation device 10a.

Continuing with the description of the operation of the sensing circuitry 83a and the electrical configuration switch 74, in one embodiment, the cardiac signals received by the terminals are conditioned by one of the capacitors 5 and filtered by one of the RF filters 7 before being provided to the input multiplexors 18 and 20, with the exception of the cardiac signals received by $A_R$ TIP 42 and $A_R$ RING 59. The cardiac signals received by $A_R$ TIP 42 and $A_R$ RING 59 are not provided to any multiplexor.

Input multiplexors 18 and 20 each selects one of the cardiac signals received by $V_R$ COIL 56, $V_R$ TIP 52, and $V_R$ RING 54.

The cardiac signals received by $A_R$ TIP 42 and $A_R$ RING 59 and are then filtered by passive filter 22 before being amplified by amplifier 26. The cardiac signal selected by input multiplexor 18 and the cardiac signal selected by input multiplexor 20 are filtered by passive filter 24 before being amplified by amplifier 28.

The outputs of the sensing circuitry 83a in FIG. 3 are provided to microcontroller 60, which, in turn, is able to trigger or inhibit the atrial and ventricular pulse generators (70 and 72, respectively, in FIG. 2) in a demand fashion in response to the absence or presence of cardiac activity as indicated by the receipt of cardiac signals at the terminals. The sensing circuitry 83a also receives control signals 86 and 88 (FIG. 2) from the microcontroller 60 for purposes of measuring cardiac performance at appropriate times, controlling gain, threshold, and polarization charge removal functionality, and controlling timing of any blocking functionality at the inputs of the sensing circuitry. Additionally, microcontroller 60 controls multiplexors 18 and 20, shown in FIG. 3, via control signal 80.

Particular Embodiments

As discussed above, the stimulation device 10a with its various components shown in FIGS. 1, 2, and 3, cannot provide bi-ventricular pacing and sensing (i.e., pacing and sensing in both the right and left ventricles of the heart 12) without modification.

There are at least three solutions, however, for enabling stimulation device 10a to accomplish bi-ventricular pacing and sensing:

1) employ a header or Y-adaptor to combine a pacing and sensing lead for the right ventricle with an added pacing and sensing lead for the left ventricle;
2) provide a separate ventricular pulse generator circuit and sensor circuit specifically for the left ventricle; and
3) add at least two additional terminals to the stimulation device, at least one additional lead from the stimulation device to associated electrodes in the heart, and a group of switches to the output path of the ventricular pacing circuitry. The third solution offers the following advantages:
   (1) the ability to sense in only a selected ventricle (for example, during a tachycardia episode, a patient may require sensing only in the right ventricle);
   (2) compatibility with the sensing/detection algorithms that rely on sensing in the right ventricle only;
   (3) the ability to pace in a selected ventricle with independent amplitude and pulse width (for example, the left ventricle may require more energy to pace);
   (4) the ability to measure a pacing threshold in only a selected ventricle; and
   (5) the ability to pace both the right and left ventricles with an interventricular delay (for example, in some cases, the left ventricle may require stimulation sooner than the right ventricle).

Figure 4:
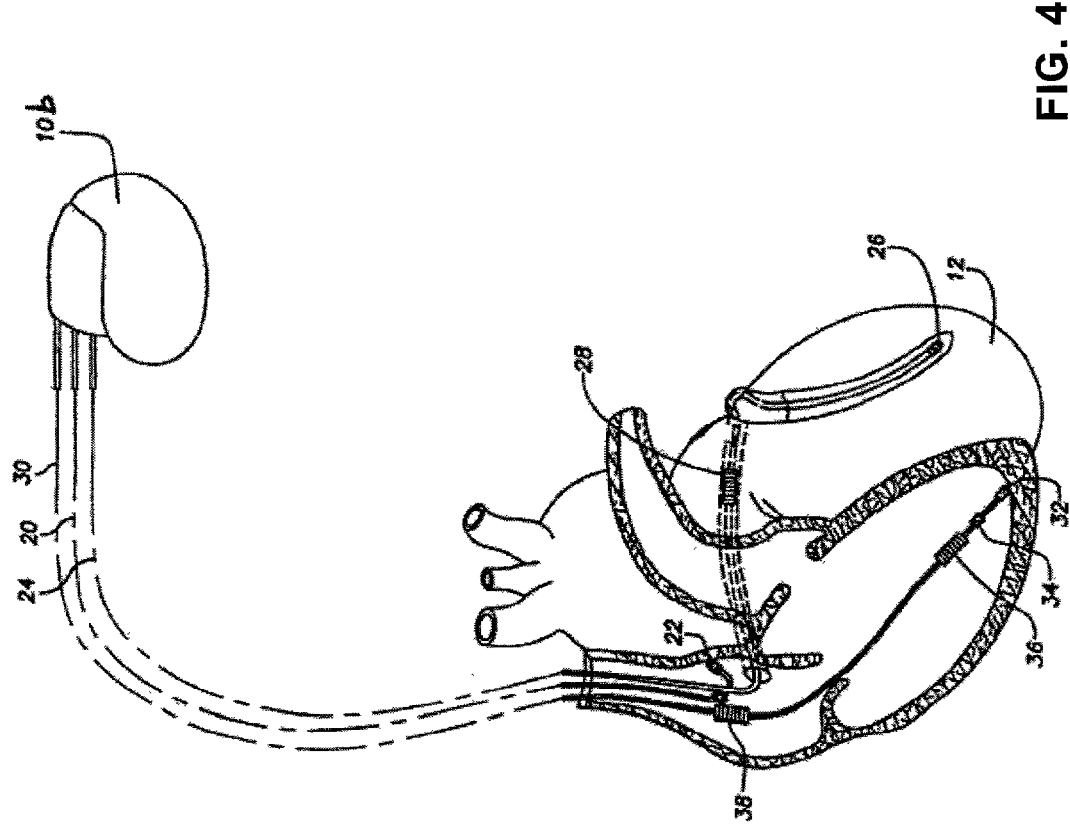
FIG. 4 is a simplified diagram illustrating an implantable stimulation device in electrical communication with three leads implanted into a patient's heart for delivering stimulation and shock therapy to both the right and left sides of the heart, according to an embodiment of the present invention.
Figure 5:
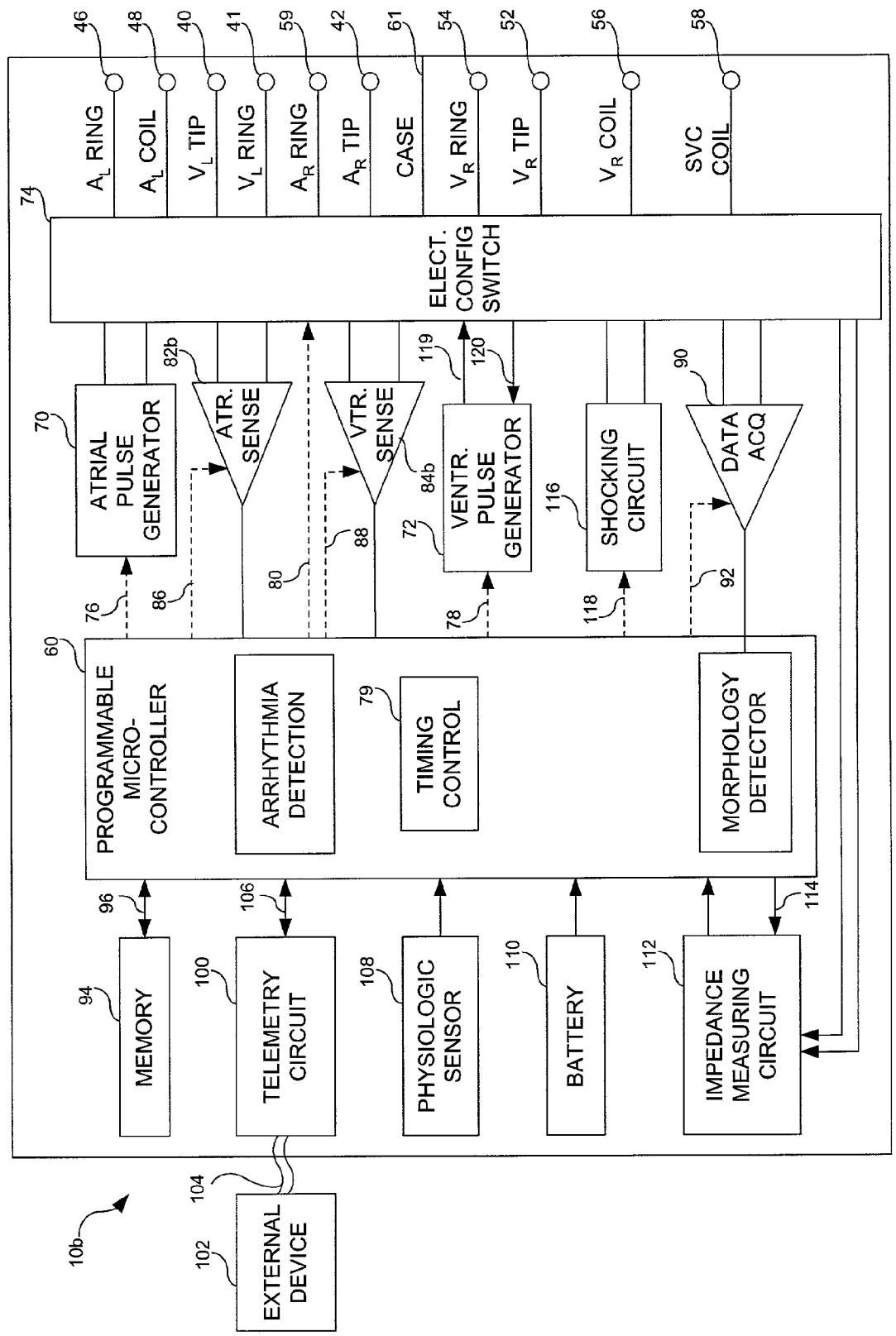
FIG. 5 is a functional block diagram of an implantable stimulation device illustrating the basic elements of a stimulation device which can provide cardioversion, defibrillation and pacing stimulation to both the right and left sides of the heart, according to an embodiment of the present invention.
Figure 6:
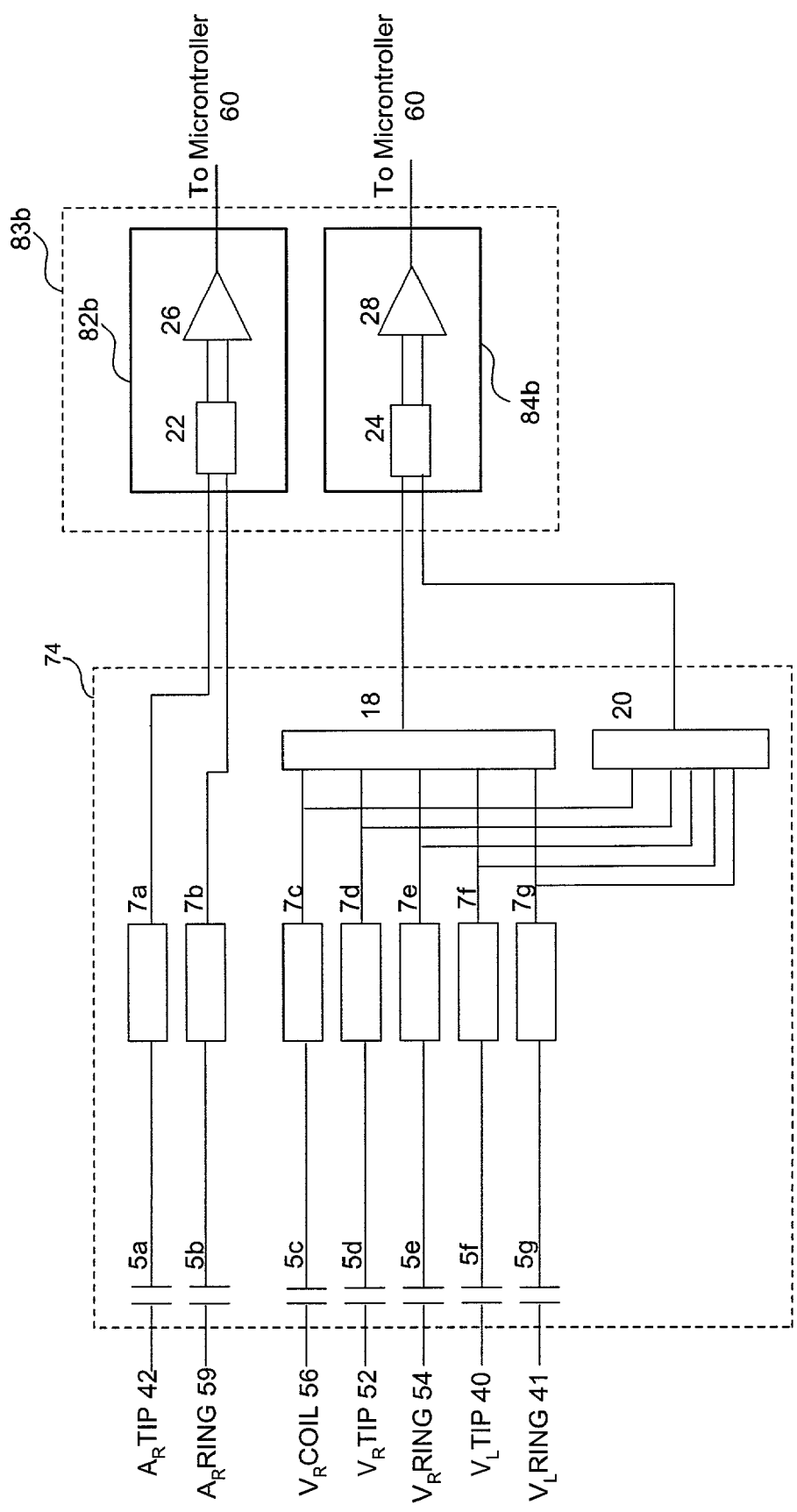
FIG. 6 is a circuit diagram of the electrical configuration switch and sense circuits of an implantable stimulation device capable of sensing in both the right and left sides of the heart, according to an embodiment of the present invention.

FIGS. 4, 5 and 6 are used to explain the third solution for bi-ventricular pacing, according to embodiments of the present invention. As shown, stimulation device 10b (also referred to as a pacing device, or a pacing apparatus) is in electrical communication with a patient's heart 12 by way of three leads, 20, 24, and 30, suitable for delivering stimulation and shock therapy to both the right and left side of the heart. Leads 20 and 30 were discussed briefly in the description of FIG. 1. A coronary sinus lead 24 has been added. Each of these leads will be discussed in a little more detail below.

To sense atrial cardiac signals and to provide right atrial stimulation therapy, the stimulation device 10b is coupled to an implantable right atrial lead 20 having at least a right atrial tip electrode 22, which typically is implanted in the patient's right atrial appendage.

To enable stimulation device 10b to perform bi-ventricular pacing, a coronary sinus lead 24 is coupled to stimulation device 10b and extends to the heart to sense left atrial and ventricular cardiac signals and to provide left-chamber pacing therapy. The coronary sinus lead 24 is designed for placement in the "coronary sinus region" via the coronary sinus. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Coronary sinus lead 24 is designed to receive atrial and ventricular cardiac signals and to deliver left ventricular pacing therapy using at least a left ventricular tip electrode 26 and shocking therapy using at least a left atrial coil electrode 28. In addition, coronary sinus lead 24 is designed to pace and sense the left ventricle using left ventricular tip electrode 26.

The stimulation device 10b is also shown in electrical communication with the patient's heart 12 by way of an implantable right ventricular (RV) lead 30 having, in this embodiment, a right ventricular tip electrode 32, a right ventricular ring electrode 34, a right ventricular coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

FIG. 5 shows a simplified block diagram of the implantable stimulation device 10b of FIG. 4, including the components that can provide cardioversion, defibrillation and pacing stimulation to both the right and left ventricles of the heart (i.e., bi-ventricular pacing), according to embodiments of the present invention. The operation of most components of the block diagram shown in FIG. 5 is similar to the operation of the components of the block diagram shown in FIG. 2. Thus, operation of those components will not be described in detail.

To enable the circuit shown in FIG. 5 to perform bi-ventricular pacing and sensing in accordance with the present invention, two additional terminals are added to the output path 119 of the ventricular pulse generator 72 to also enable pacing and sensing in the left ventricle of the heart. As will be described below, this allows for bi-ventricular pacing and sensing while also allowing the realization of the many advantages discussed above.

To achieve left ventricle sensing, pacing, and shocking, the implantable stimulation device 10b further includes a left ventricular tip terminal ($V_L$ TIP) 40 and a left ventricular ring terminal ($V_L$ RING) 41, for example, which are adapted for connection to the left ventricular tip electrode 26 and the left ventricular ring electrode 29 (shown in FIG. 4). The additional terminals also allow relevant data to be transmitted to telemetry circuit 100. To achieve left atrium sensing, pacing and shocking, the connector also includes at least a left atrial ring terminal ($A_L$ RING) 46 and a left atrial shocking terminal ($A_L$ COIL) 48, which are adapted for connection to the left atrial tip electrode 27, and the left atrial coil electrode 28, respectively.

FIG. 6 is a circuit diagram of electrical configuration switch 74 and sensing circuitry 83b. The sensing circuitry 83b illustrated in FIG. 6 represents a modified version of the sensing circuitry illustrated in FIG. 3. As shown in FIG. 6, multiplexors 18 and 20 can now select from two additional inputs (i.e., $V_L$ TIP 40 and $V_L$ RING 41). This allows sensing in the left ventricle as well as the right ventricle of the heart (i.e., bi-ventricular sensing) while also allowing the realization of the many advantages mentioned above.

Switch Configurations

Figure 7A:
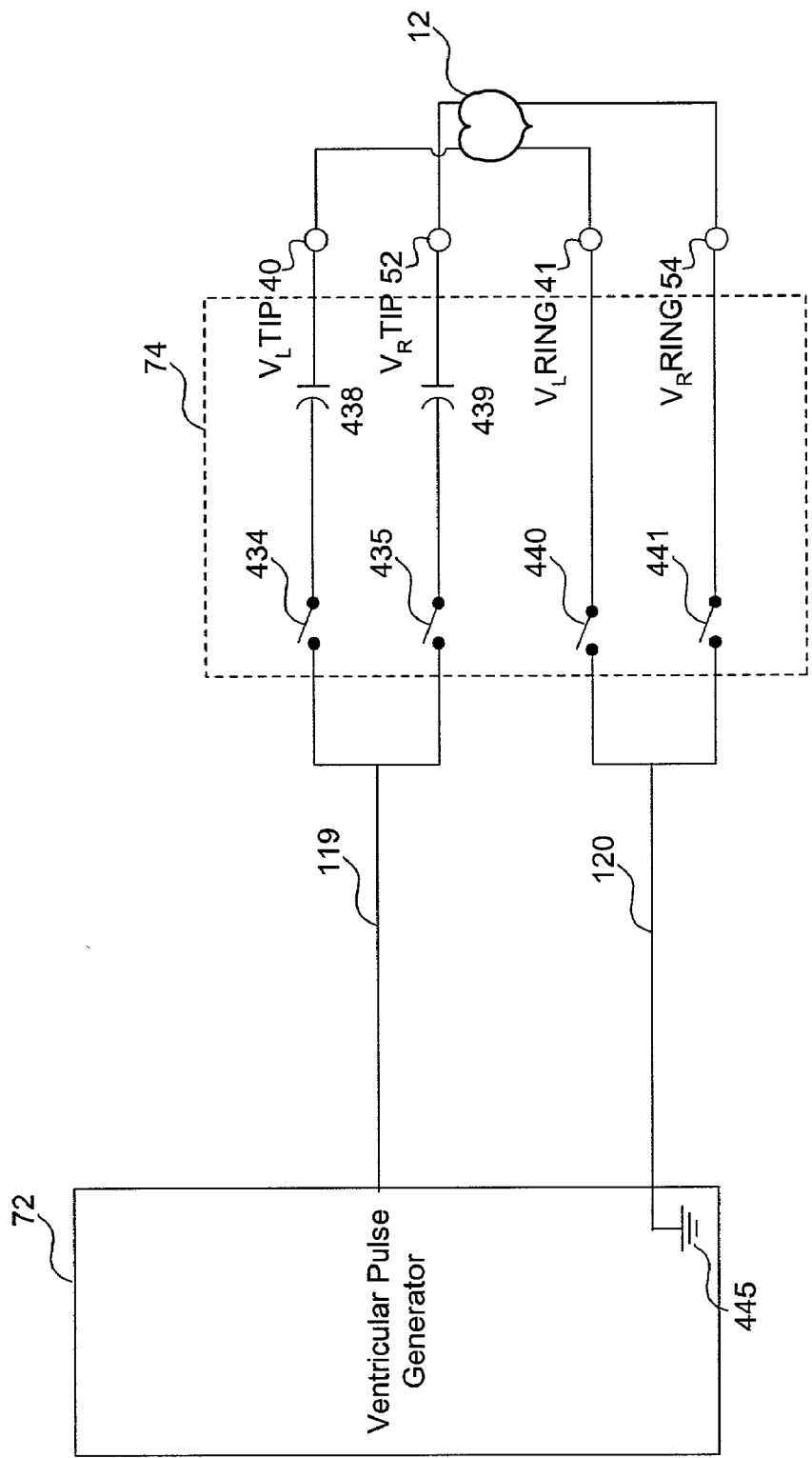

FIG. 7A illustrates the pacing circuitry of implantable stimulation device 10b capable of pacing in both the right and left sides of the heart according to an embodiment of the present invention. More specifically, FIG. 7A shows ventricular pulse generator 72, output path 119, return path 120, switches 434, 435, 440 and 441, terminals $V_L$ TIP 40, $V_R$ TIP 52, $V_L$ RING 41, $V_R$ RING 54, capacitors 438 and 439, ground 445, and heart 12. Bi-ventricular pacing is accomplished by the addition of (and control of) switches 434 and 435 to output path 119, and switches 440 and 441 to return path 120, of ventricular pulse generator 72.

In one embodiment, switches 434, 435, 440 and 441 are located within electrical configuration switch 74. In yet another embodiment, the switches are located external to electrical configuration switch 74.

Terminals $V_L$ TIP 40, $V_R$ TIP 52, $V_L$ RING 41, and $V_R$ RING 54 (in FIG. 7A) represent the same terminals shown in the sensing circuitry of FIG. 6. As described above, these terminals are located within the stimulation device 10b. These terminals are connected to their respective electrodes located within heart 12 via respective leads, as shown in FIG. 4.

In FIG. 7A, switches 434, 435, 440, and 441 are all shown as being open. As will be described below, all or a selected combination of switches 434, 435, 440, and 441, can be closed to enable only left ventricular pacing, only right ventricular pacing, or bi-ventricular pacing, as shown in the series of configurations illustrated in FIGS. 7B–7F.

Single Ventricular (LV or RV) Pacing

In both FIGS. 7B and 7C, switches 434, 435, 440, and 441 are configured for left ventricular pacing only. In FIG. 7B switches 434 and 440 are closed, and switches 435 and 441 are open. In FIG. 7C switches 434 and 441 are closed, and switches 435 and 440 are open. In both configurations, a pulse produced by ventricular pulse generator 72 is delivered through terminal $V_L$ TIP 40 to left ventricular tip electrode 32, thereby causing stimulation (i.e., pacing) of the left ventricle. However, in the configuration of FIG. 7B the left ventricular ring electrode 29 (coupled to terminal $V_L$ RING 41) acts as the return electrode. In contrast, in the configuration of FIG. 7C the return electrode is right ventricular ring electrode 34 (coupled to terminal $V_R$ RING 54).

Referring now to FIGS. 7D and 7E, in both of these figures switches 434, 435, 440 and 441 are configured for right ventricular pacing only. In FIG. 7D switches 435 and 441 are closed, and switches 434 and 440 are open. In FIG. 7E switches 435 and 440 are closed, and switches 434 and 441 are open. In both configurations, a pulse produced by ventricular pulse generator 72 is delivered through terminal $V_R$ TIP 52 to right ventricular tip electrode 32, thereby causing stimulation (i.e., pacing) of the right ventricle. However, in the configuration of FIG. 7D the right ventricular ring electrode 34 (coupled to $V_R$ RING 54) acts as the return electrode. In contrast, in the configuration of FIG. 7E the return electrode is left ventricular ring electrode 29 (coupled to terminal $V_L$ RING 41). In an alternative embodiment, with the exception of the configurations illustrated in FIGS. 7C and 7E, the return electrode can be the case electrode 61 (shown in FIG. 5). This configuration is a unipolar pacing configuration.

Simultaneous Bi-Ventricular (LV and RV) Pacing

Figure 7F:
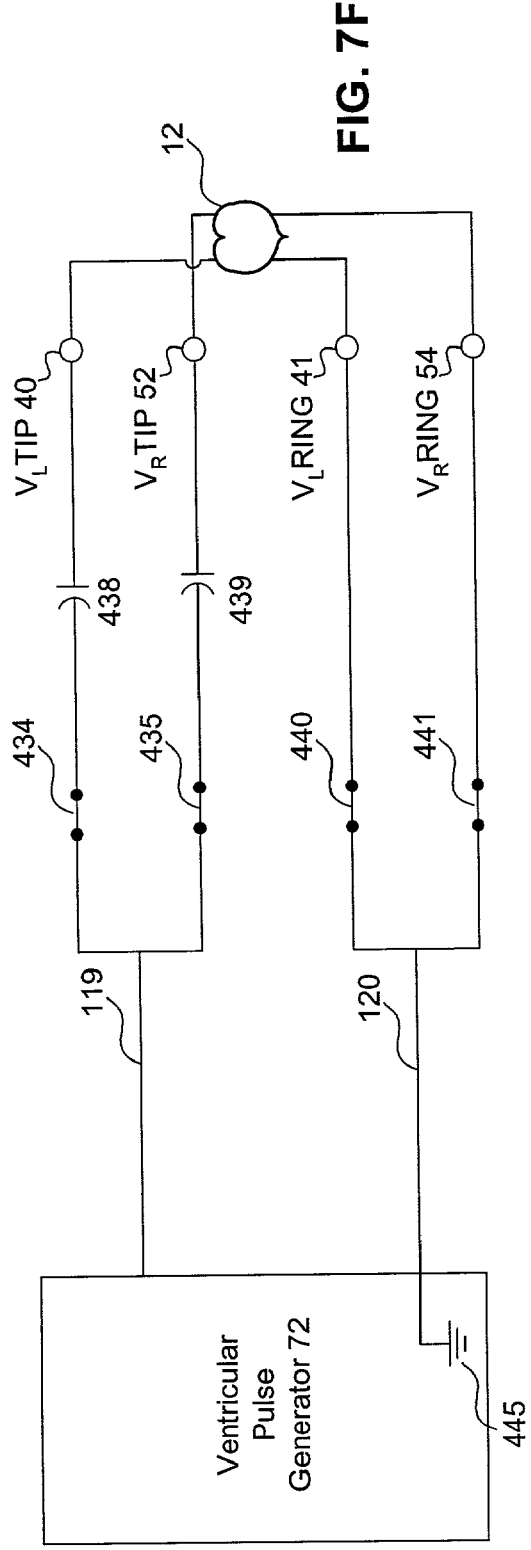
Figure 7G:
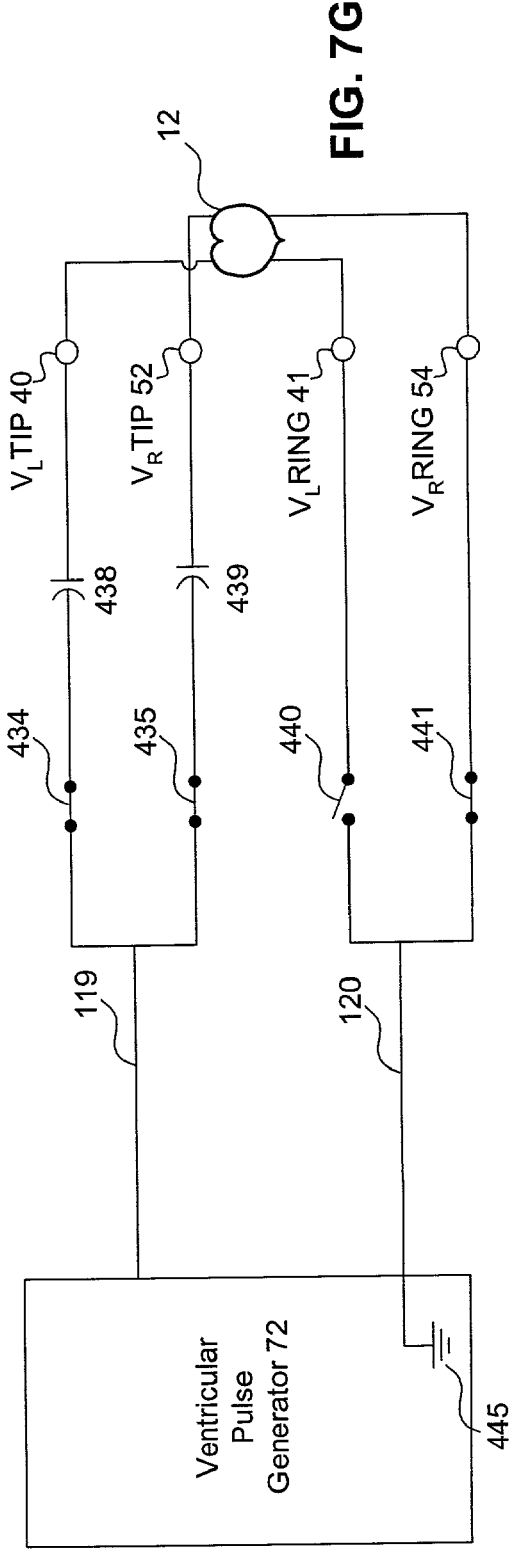

In both FIGS. 7F and 7G, switches 434, 435, 440, and 441 are configured for bi-ventricular pacing. In FIG. 7F switches 434, 435, 440, and 441 are all closed. In FIG. 7G switches 434, 435 and 441 are closed, and switch 440 is open. In both configurations, a pulse produced by ventricular pulse generator 72 is delivered through terminal $V_L$ TIP 40 to left ventricular tip electrode 26, and through terminal $V_R$ TIP 52 to right ventricular tip electrode 32, thereby causing simultaneous stimulation (i.e., pacing) of both the left ventricle and the right ventricle. In the configuration of FIG. 7F the left ventricular ring electrode 29 (coupled to terminal $V_L$ RING 41) and right ventricular ring electrode 34 (coupled to terminal $V_R$ RING 54) both act as return electrodes. In the configuration of FIG. 7G the return electrode is right ventricular ring electrode 34 (coupled to terminal $V_R$ RING 54). In another configuration (not shown), switch 440 is closed and switch 441 is open so that the left ventricular ring electrode 29 (coupled to terminal $V_L$ RING 41) acts as the return electrode. In an alternative embodiment, with the exception of the configurations illustrated in FIGS. 7C and 7E, the return electrode can be the case electrode 61 (shown in FIG. 5). This configuration is a unipolar pacing configuration. The configurations of FIGS. 7F and 7G (and the just mentioned not shown configuration) allow a patient requiring stimulation in both the right and left ventricles to benefit by providing the capability to simultaneously pace both the left ventricle and the right ventricle.

Bi-Ventricular (LV and RV) Pacing with an Interventricular Delay

Ideally, the left and right ventricle of the heart should contract at the same time. A large portion of the population, however, has an enlarged left side of the heart. This enlargement results in failure of the left ventricle to contract with the right ventricle. Therefore, the left ventricle may need to be stimulated sooner than the right ventricle. The present invention enables a patient with this problem, for example, to receive the necessary therapy. More specifically, the present invention can be used for bi-ventricular pacing with an interventricular delay, as illustrated in FIGS. 7H and 7I.

Referring now to FIG. 7H, at time V1, switches 434 and 440 are closed, and switches 435 and 441 are open. At time V1, a first pacing pulse produced by ventricular pulse generator 72 is delivered through terminal $V_L$ TIP 40 to left ventricular tip electrode 26, thereby causing stimulation (i.e., pacing) of the left ventricle. The left ventricular ring electrode 29 (coupled to terminal $V_L$ RING 41) acts as the return electrode, at time V1.

At a different time V2, switches 435 and 441 are closed, and switches 434 and 440 are opened. A second pacing pulse produced by ventricular pulse generator 72 is then delivered through terminal $V_R$ TIP 52 to right ventricular tip electrode 32, thereby causing stimulation to the right ventricle. The right ventricular ring electrode 34 (coupled to terminal $V_R$ RING 54) acts as the return electrode, at time V2.

FIG. 7I also illustrates bi-ventricular pacing with an interventricular delay. In FIG. 7I, at time V1, switches 434 and 441 are closed, and switches 435 and 440 are open. Right ventricular ring electrode 34 (coupled to terminal $V_R$ RING 54) acts as the return electrode.

At a different time V2, switches 435 and 441 are closed, and switches 434 and 440 are opened. Right ventricular ring electrode 34 (coupled to terminal $V_R$ RING 54) acts as the return electrode.

In both FIGS. 7H and 7I, microcontroller 60 can control switching, and thus, can control various pacing parameters, such as AV delay, RV-LV delay, V—V delay, etc.

Pacing in a Selected Ventricle with Independent Amplitude and Pulse Width

One ventricle may need more stimulation than the other. The present invention enables a patient requiring such treatment to receive the necessary therapy. More specifically, the amplitude and pulse width of the pulses provided to the left and right ventricles can be independently controlled.

This can be accomplished, for example, by providing a first pacing pulse having a first amplitude and a first width to the left ventricle, at time V1, followed by a second pacing pulse delivered to the right ventricle, at time V2, having a second amplitude and a second width. It is noted, that there will be a delay between the first pacing pulse and the second pulse. However, as discussed above, this may be beneficial and purposefully selected. Because the present invention accomplishes bi-ventricular pacing using a single ventricular pulse generator 72, it may not be possible to simultaneously pace the left and right ventricle with pacing pulses of different amplitude and width. That is, if simultaneous bi-ventricular pacing is desired, the pacing pulse delivered to the left ventricle and right ventricle will have the same amplitude and height.

CONCLUSION

While various embodiments of the invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus the invention should not be limited by any of the above-described exemplary embodiments, but should be defined only in accordance with the following claims and their equivalents.

What is claimed is:

1. An implantable cardiac stimulation device, comprising:
   a first terminal for connection to a left ventricular pacing electrode, said left ventricular pacing electrode for placement in electrical contact with a left ventricle;
   a second terminal for connection to a right ventricular pacing electrode, said right ventricular pacing electrode for placement in a right ventricle;
   a pulse generator;
   switch means for connecting any combination of said first and second terminals to said pulse generator to deliver electrical therapy to said left ventricular pacing electrode, said right ventricular pacing electrode, or both said left and right ventricular pacing electrodes;
   wherein said switch means comprises:
     a first switch connecting said pulse generator to said first terminal; and
     a second switch connecting said pulse generator to said second terminal; and
   control means for controlling operation of said pulse generator and said switch means;
   wherein said control means comprises:
     a programmable microcontroller; and
     computer readable program code means for causing said microcontroller to control said switch means to close only one of said first and second switches to provide left ventricular pacing to a heart, to close only the other of said first and second switches to provide right ventricular pacing, and to close both of said first and second switches at differing times to provide bi-ventricular pacing with an interventricular delay.

2. The cardiac stimulation device of claim 1, further comprising a third terminal and a fourth terminal, wherein said switch means further comprises:
   means for connecting any combination of said third terminal and said fourth terminal to ground to provide a return path for said electrical therapy from a left ventricular ring electrode, a right ventricular ring electrode, or both said left and right ventricular ring electrodes.

3. The cardiac stimulation device of claim 1, wherein said switch means comprises:
   a third switch connecting said pulse generator to said third terminal; and
   a fourth switch connecting said pulse generator to said fourth terminal.

4. The cardiac stimulation device of claim 3,
   wherein said computer readable program code means for causing said microcontroller to control said switch means to
   provide left ventricular pacing by closing only one of said first and second switches and closing at least one of said third and fourth switches,
   provide right ventricular pacing by closing only the other of said first and second switches and closing at least one of said third and fourth switches, and
   provide bi-ventricular pacing by closing both of said first and second switches and closing at least one of said third and fourth switches.

5. The cardiac stimulation device of claim 1, further comprising a third terminal and a fourth terminal, wherein said switch means further comprises:
   means for connecting any combination of said third terminal and said fourth terminal to ground to provide a return path for said electrical therapy from an additional pacing electrode, a case of said stimulation device, or both said additional pacing electrode and said case.

6. The cardiac stimulation device of claim 1, wherein said left ventricular pacing electrode is a tip electrode, and wherein said right ventricular pacing electrode is a tip electrode.

7. The cardiac stimulation device of claim 1, wherein said programmable microcontroller independently controls pacing pulse amplitude and pacing pulse width to the left and right ventricles.

8. A method for operating a cardiac stimulation device having a first terminal for connection to a right ventricular pacing electrode, a second terminal for connection to a left ventricular pacing electrode, and a third terminal, the method comprising:
   using a pulse generator to generate an electrical pulse for delivery to a heart;
   electrically configuring switch means to deliver said electrical pulse to the first terminal when pulse delivery is desired to a right ventricle of the heart, said switch means comprising closing a first switch to connect said pulse generator to the first terminal and opening a second switch to isolate said pulse generator from the second terminal;
   electrically configuring said switch means to deliver said electrical pulse to the second terminal when pulse delivery is desired to a left ventricle of the heart, said switch means comprising opening said first switch to isolate said pulse generator from the first terminal and closing the second switch to connect said pulse generator to the second terminal; and
   electrically configuring said switch means to deliver said electrical pulse to both the first and second terminals when bi-ventricular pulse delivery is desired, said switch means comprising closing the first switch at a time $t_0$ to connect said pulse generator to the first terminal, closing the second switch at a time $t_1$ to connect said pulse generator to the second terminal wherein $t_0$ differs from $t_1$ to provide bi-ventricular pacing with an interventricular delay.

9. The method of claim 8, further comprising:
   electrically configuring said switch means to connect any combination of said third terminal and a fourth terminal to ground to provide a return path for said electrical pulse from a right ventricular ring electrode, a left ventricular ring electrode, or both the right and left ventricular ring electrodes.

10. The method of claim 9, wherein said fourth configuring step comprises:
  closing a third switch to connect said pulse generator to the third terminal; and
  opening a fourth switch to isolate said pulse generator from the fourth terminal.

11. The method of claim 9, wherein said fourth configuring step further comprises:
  opening a third switch to isolate said pulse generator from the third terminal; and
  closing a fourth switch to connect said pulse generator to the fourth terminal.

12. The method of claim 9, wherein said fourth configuring step further comprises:
  closing a third switch to connect said pulse generator to the third terminal; and
  closing a fourth switch to connect said pulse generator to the fourth terminal.

13. An implantable cardiac stimulation device, comprising:
  a pulse generator;
  a left ventricular pacing electrode switchably coupled to said pulse generator;
  a right ventricular pacing electrode switchably coupled to said pulse generator;
  a switching system to connect any combination of said left ventricular pacing electrode and said right ventricular pacing electrode to deliver pacing pulses to a left ventricle, a right ventricle, or both the left and right ventricles; and
  a controller to control operation of said pulse generator and said switching system;
  wherein said controller causes said switching system to close only one of said first and second switches to provide left ventricular pacing to a heart, to close only the other of said first and second switches to provide right ventricular pacing, and to close both of said first and second switches at differing time to provide bi-ventricular pacing with an interventricular delay.

14. The cardiac stimulation device of claim 13, further comprising:
  a first terminal for connection to said left ventricular pacing electrode; and
  a second terminal for connection to said right ventricular pacing electrode;
  wherein said switching system comprises:
    a first switch to connect said pulse generator to said first terminal; and
    a second switch to connect said pulse generator to said second terminal.

15. The cardiac stimulation device of claim 13, wherein said pacing pulses have a pulse amplitude and pulse width, and wherein said controller independently controls said pulse amplitude and said pulse width to the left and right ventricles.

* * * * *